(12) United States Patent
Higashi et al.

(10) Patent No.: US 6,624,325 B1
(45) Date of Patent: Sep. 23, 2003

(54) CATALYST FOR USE IN PRODUCING LOWER FATTY ACID ESTER, PROCESS FOR PRODUCING THE CATALYST, AND PROCESS FOR PRODUCING LOWER FATTY ACID ESTER USING THE CATALYST

(75) Inventors: Tomoyoshi Higashi, Oita (JP); Kousuke Narumi, Oita (JP); Hideyuki Kamei, Oita (JP); Hiroshi Uchida, Oita (JP)

(73) Assignee: Showa Denko K. K., Tokyo (JP)

( * ) Notice: Subject to any disclaimer, the term of this patent is extended or adjusted under 35 U.S.C. 154(b) by 299 days.

(21) Appl. No.: 09/582,653

(22) PCT Filed: Jun. 1, 2000

(86) PCT No.: PCT/JP00/03570

§ 371 (c)(1),
(2), (4) Date: Jun. 29, 2000

(87) PCT Pub. No.: WO00/74842

PCT Pub. Date: Dec. 14, 2000

Related U.S. Application Data

(60) Provisional application No. 60/141,249, filed on Jun. 30, 1999.

(30) Foreign Application Priority Data

Jun. 3, 1999 (JP) ............................................. 11-156060

(51) Int. Cl.[7] .......................... C07C 69/02; C07C 67/04
(52) U.S. Cl. ...................................... 560/231; 560/247
(58) Field of Search ............................... 502/305, 311; 560/231, 247

(56) References Cited

U.S. PATENT DOCUMENTS 5,861,530 A    1/1999  Atkins et al.
6,043,184 A  * 3/2000  Karmakar et al. .......... 502/208

FOREIGN PATENT DOCUMENTS

| CN | 1150585 A | 5/1997 |
|---|---|---|
| EP | 0 333 076 A1 | 9/1989 |
| EP | 0 375 267 A2 | 6/1990 |
| EP | 0 469 719 A1 | 2/1992 |
| EP | 0 562 139 A1 | 9/1993 |
| EP | 0 757 027 A1 | 2/1997 |
| EP | 0 775 520 A2 * | 5/1997 |
| JP | A-4-139148 | 5/1992 |
| JP | A-4-139149 | 5/1992 |
| JP | A-5-65248 | 3/1993 |
| JP | A-5-163200 | 6/1993 |
| JP | A-5-170699 | 7/1993 |
| JP | A-5-255185 | 10/1993 |
| JP | A-5-294894 | 11/1993 |
| JP | A-6-72951 | 3/1994 |
| JP | A-9-118647 | 5/1997 |

* cited by examiner

*Primary Examiner*—Mukund J. Shah
*Assistant Examiner*—Zachary C. Tucker
(74) *Attorney, Agent, or Firm*—Sughrue Mion, PLLC

(57) ABSTRACT

A catalyst for producing lower fatty acid esters through esterification of a lower aliphatic carboxylic acid with a lower olefin, comprising a heteropoly acid or a, salt thereof held on a carrier, and having a specific surface area of the catalyst, as measured by a BET method, of 65 $m^2/g$-350 $m^2/g$. A process for producing the catalyst and a process for producing a lower fatty acid ester by using the catalyst are also provided.

8 Claims, No Drawings

CATALYST FOR USE IN PRODUCING LOWER FATTY ACID ESTER, PROCESS FOR PRODUCING THE CATALYST, AND PROCESS FOR PRODUCING LOWER FATTY ACID ESTER USING THE CATALYST

CROSS REFERENCE TO RELATED APPLICATIONS

This application is an application is a national stage entry filed under 35 U.S.C. 0371 of PCT/JP00/03570, filed Jun. 1, 2000, which is claiming benefit pursuant to 35 U.S.C. § 119(e) (1) of the filing date of the Provisional Application 60/141,249 filed Jun. 30, 1999, pursuant to 35 U.S.C. § 111(b).

TECHNICAL FIELD

The present invention relates to a catalyst for producing lower fatty acid esters, through a reaction between a lower aliphatic carboxylic acid and a lower olefin; a process for producing the catalyst; and a process for producing lower fatty acid esters by using the catalyst.

BACKGROUND ART

A reaction between a lower olefin and a lower aliphatic carboxylic acid in the presence of an acidic catalyst is known to yield the corresponding lower fatty acid ester. In addition, a heteropoly acid and a salt thereof are known to serve as an effective catalyst for the reaction. For example, Japanese Unexamined Patent Publications (Kokai) No. 4-139148, No. 4-139149, No. 5-65248, No. 5-163200, No. 5-170699, No. 5-255185, No. 5-294894, No. 6-72951, and No. 9-118647 disclose conventional techniques in relation to the above process and catalyst.

In these techniques, catalyst components and reaction conditions are elaborated from various aspects, and lower fatty acid esters can be produced with a comparatively high yield. However, nowadays, there is a demand for a catalyst having higher performance and a higher activity per unit time.

Among these publications, Japanese Unexamined Patent Publications (Kokai) No. 5-294894 and No. 9-118647 disclose a so-called supported catalyst in which a heteropoly acid and/or a salt thereof serving as an active component are held on a carrier formed of a porous substance such as silica gel.

In general, the catalytic properties of a produced supported catalyst depend on the type and properties of the carrier for supporting the catalyst component. In addition, the catalyst performance, such as catalytic activity or selectivity of a target product during reaction, varies depending on the properties of the produced supported catalyst.

The aforementioned Japanese Unexamined Patent Publications (Kokai) No. 5-294894 and No. 9-118647 fail to provide detailed discussion of a carrier, and furthermore, do not disclose the catalytic performance of a prepared supported catalyst, particularly performance attributed to the properties of the carrier.

DISCLOSURE OF INVENTION

In view of the foregoing, an object of the present invention is to provide a catalyst having higher catalytic activity in a process for producing a lower fatty acid ester through esterification of a lower olefin with a lower aliphatic carboxylic acid in the presence of a catalyst wherein at least one compound selected from heteropoly acids and salts thereof is caused to be held on a carrier. Another object of the invention is to provide a process for producing the catalyst. Still another object of the invention is to provide a process for producing a lower fatty acid ester by using the catalyst.

The present inventors have conducted intensive studies to obtain a catalyst which has high performance and is useful for producing lower fatty acid esters through reaction of a lower olefin and a lower aliphatic carboxylic acid.

Thus, the present inventors have found that the catalytic activity of a supported catalyst used in the above reaction containing a heteropoly acid and/or a salt thereof can be improved remarkably when the specific surface area of the catalyst, as measured by a BET method, falls within a specific range. The present invention has been accomplished on the basis of this finding.

Accordingly, the present invention (I) provides a catalyst for producing a lower fatty acid ester which catalyst contains at least one compound selected from heteropoly acids and salts thereof, which compound is caused to be held on a carrier and which catalyst is used in a process for producing a lower fatty acid ester through esterification of a lower aliphatic carboxylic acid with a lower olefin, wherein the specific surface area of the catalyst, as measured by a BET method, is 65 $m^2/g$–350 $m^2/g$.

The present invention (II) provides a catalyst according to the present invention (I) used for producing a lower fatty acid ester, which catalyst has a specific surface area of the carrier as measured by BET method of 100 $m^2/g$–500 $m^2/q$.

The present invention (III) provides a process for producing the catalyst as recited in the present invention (I) or (II) useful for producing a lower fatty acid ester.

The present invention (IV) provides a process for producing a lower fatty acid ester through esterification of a lower aliphatic carboxylic acid with a lower olefin in the presence of the catalyst as recited in the present invention (I) or (II).

BEST MODE FOR CARRYING OUT THE INVENTION

The present invention will now be described in detail.

The catalyst for producing a lower fatty acid ester according to the invention (I) will be described. The invention (I) encompasses a catalyst for producing a lower fatty acid ester, which catalyst contains at least one compound selected from heteropoly acids and salts thereof, which compound is caused to be held on a carrier and which catalyst is used in a process for producing a lower fatty acid ester through esterification of a lower aliphatic carboxylic acid with a lower olefin, wherein the specific surface area of the catalyst, as measured by a BET method, is 65 $m^2/g$–350 $m^2/g$.

The heteropoly acids used in the invention (I) comprise a hetero element and poly elements bonded to oxygen. The hetero element is typically silicon or phosphorus, but is not limited thereto, and can be optionally selected from elements belonging to Groups 1–17 in the periodic table (Nomenclature of Inorganic Chemistry by International Union of Pure and Applied Chemistry, revised edition (1989); the same applies hereinafter).

The hetero element is not particularly limited, and examples thereof include a cupric ion; a divalent ion of beryllium, zinc, cobalt, or nickel; a trivalent ion of boron, aluminum, gallium, iron, cerium, arsenic, antimony, phosphorus, bismuth, chromium, or rhodium; a tetravalent ion of silicon, germanium, tin, titanium, zirconium, vanadium, sulfur, tellurium, manganese, nickel, platinum, thorium, hafnium, cerium, or other rare earth metals; a pentavalent ion of phosphorus, arsenic, vanadium, or antimony; a hexavalent tellurium ion; and a heptavalent iodine ion.

The poly element is not particularly limited, and examples thereof include tungsten, molybdenum, vanadium, niobium, and tantalum.

Such a heteropoly acid is well known as "a polyoxo anion," "a polyoxo metal salt," or "an oxidized metal cluster." Some structures of the well-known anions are named after researchers in this field, such as the Keggin structure, the Dawson structure, and the Anderson-Evans-Pearov structure. A heteropoly acid typically has a high molecular weight, e.g., a molecular weight of 700–8500, and also encompasses a dimer complex thereof.

No particular limitation is imposed on the heteropoly-acid salt, and a metal salt or an onium salt may be used so long as a portion of or all hydrogen atoms of the heteropoly-acid are substituted. Non-limitative examples include metal salts of lithium, sodium, potassium, cesium, magnesium, barium, copper, gold, and gallium; and onium salts such as ammonium salts.

A heteropoly acid compound, particularly when in the form of a free acid or a salt, has comparatively high solubility to a polar solvent such as water or a oxygen-containing compound solvent, and the solubility thereof can be controlled by the selection of a suitable counter ion of the salt.

Examples of heteropoly acids which can be used in the present invention include the following compounds:

| | |
|---|---|
| silicotungstic acid | $H_4[SiW_{12}O_{40}] \cdot xH_2O$; |
| phosphotungstic acid | $H_3[PW_{12}O_{40}] \cdot xH_2O$; |
| phosphomolybdic acid | $H_3[PMo_{12}O_{40}] \cdot xH_2O$; |
| silicomolybdic acid | $H_4[SiMo_{12}O_{40}] \cdot xH_2O$; and |
| phosphovanadomolybdic acid | $H_{3+n}[PVnMo_{12-n}O_{40}] \cdot xH_2O$. |

Examples of particularly preferred heteropoly acid salts include lithium salts, sodium salts, potassium salts, cesium salts, magnesium salts, barium salts, copper salts, gold salts, gallium salts, and ammonium salts of the above-described particularly preferred heteropoly acids.

The amount of a heteropoly acid or a salt thereof caused to be held on a carrier is preferably 10 wt %–200 wt %, more preferably 50 wt %–150 wt % based on the weight of the carrier.

When the amount of a heteropoly acid or a salt thereof is less than 10 wt %, the amount of an active component in the catalyst may be too small, and the catalytic activity per unit weight of the catalyst might be disadvantageously lowered.

When the content of a heteropoly acid or a salt thereof is in excess of 200 wt %, coking occurs easily, and the service life of the catalyst might be disadvantageously shorter. In addition, when a heteropoly acid or a salt thereof is used in an excessively large amount, the cost of the catalyst increases, and the cost for transporting the catalyst increases due to an increase in the weight of the catalyst per unit volume.

No further limitation is imposed on the catalyst according to the invention (I), except that the catalyst for producing lower fatty acid esters must contain a heteropoly acid and/or a salt thereof serving as an active component during reaction and must have a specific surface area, as measured by a BET method, of 65 $m^2/g$–350 $m^2/g$, and any component can be added thereto so long as the component does not inhibit catalytic performance. Certainly, any third component may be added thereto so as to obtain a catalyst having higher catalytic performance. No particular limitation is imposed on the third component, and any additives, such as inorganic and organic substances, may be added.

The specific surface area of the catalyst for producing a lower fatty acid ester according to the invention (I) is predominantly measured through an adsorption method in which the specific surface area is determined from the amount of a monomolecular layer adsorbed on a solid surface by use of an adsorbent having a defined molecular cross-sectional area. A typical example of the methods is a BET method.

A BET method is a method in which the specific surface area is determined by use of the adsorption isotherm derived by Brunauer, Emmett, and Teller. The method is described in detail in "Shokubai kagaku," 115 page "3.2.3 Various forms of adsorption isotherm," and on 455 page "6.1.3 Method for measuring surface area (first edition, first printing, on Mar. 10, 1981, Tokyo Kagaku Dojin).

The specific surface area of a carrier can be measured through BET method by use of a typical gas adsorption measuring apparatus. A specific example of such an apparatus includes BELSORP 28SA (Bel Japan).

The specific surface area of the catalyst for producing a lower fatty acid ester according to the invention (I), which surface area is measured by BET method, is 65 $m^2/g$–350 $m^2/g$, preferably 100 $m^2/g$–220 $m^2/g$, more preferably 120 $m^2/g$–200 $m^2/g$.

When the specific surface area of the catalyst, as measured by a BET method, is less than 65 $m^2/g$ or in excess of 350 $m^2/g$, the space-time yield, i.e., an index of catalytic activity, is disadvantageously lowered.

No particular limitation is imposed on the substance which can be employed as the carrier of the catalyst of the invention (I), so long as the substance provides the specific surface area of the catalyst, as measured by a BET method, of 65 $m^2/g$–350 $m^2/g$ when the catalyst is prepared by causing a heteropoly acid and/or a salt thereof or any third component to be held on the carrier. Thus, porous substances, which are typically used as a catalyst carrier, may be used. Non-limitative examples include silica, diatomaceous earth, montmorillonite, titania, activated carbon, alumina, or silica-alumina.

The form of-the substance which can be employed as the carrier of the catalyst according to the invention (I) is not particularly limited, and the substance may be used in any form, such as powder, balls, or pellets.

The carrier preferably comprises a siliceous material in the form of balls or pellets. More preferably, the carrier comprises silica having a purity of 95 wt % or more as represented by weight ratio based on the total weight of the carrier.

The average particle size of the carrier material is preferably 2 mm–10 mm when used in a fixed bed, and powder to 5 mm when used in a fluidized bed, although average particle size depends on the type of reaction.

The present invention (II) will be described next.

The invention (II) provides a catalyst according to the invention (I) used for producing a lower fatty acid ester, which catalyst has a specific surface area of the carrier, as measured by a BET method, of 100 $m^2/g$–500 $m^2/g$.

In general, when a supported catalyst is produced, the specific surface area of the produced catalyst is known to become smaller than that of the carrier for producing the catalyst, depending on a selected catalyst component and method for preparation of the catalyst. Thus, the carrier which can be employed in the production of the catalyst for producing a lower fatty acid ester according to the invention (I) must have high maximum and minimum values of specific surface area as measured by BET method when a heteropoly acid and/or a salt thereof or any third component is not caused to be held on the carrier.

Specifically, in order to obtain the catalyst according to the invention (I), i.e., a catalyst having a specific surface area of 65 m$^2$/g–350 m$^2$/g, the carrier per se preferably has a specific surface area of 100 m$^2$/g–500 m$^2$/g, more preferably 200 m$^2$/g–310 m$^2$/g.

In a supported catalyst in which a catalyst component is caused to be held on a carrier, the specific surface area corresponding to the catalyst component increases. Although a variety of effects are provided by a catalyst carrier, it is generally known that the specific surface area of a catalyst component increases, to thereby increase the area contacting a reactive substance and the catalytic activity.

The catalyst according to the invention (II) is considered to be subjected to the above effect. Thus, when a carrier having a specific surface area less than 100 m$^2$/g is used, the prepared catalyst per se hardly has a specific surface area of 65 m$^2$/g or higher. In this case, the effect of improving catalytic activity disadvantageously decreases.

In contrast, when the specific surface area of a carrier is in excess of 500 m$^2$/g, the carrier disadvantageously possesses low mechanical strength. In general, as described above, the larger the specific surface area of a catalyst component, the higher the catalytic activity. In other words, the catalytic activity of a catalyst is presumed to increase with the increase of the specific surface area of a carrier. However, surprisingly, the catalytic activity of the catalyst according to the invention (II) tends to decrease when the specific surface area of the carrier exceeds 500 m$^2$/g.

The mechanism of this phenomenon has not been elucidated in detail. Presumably, one possible mechanism is that a heteropoly acid or a salt thereof plugs micropores of the carrier due to the comparatively large size of the molecule to cause insufficient performance of the catalyst, since the size of micropores decreases in proportion to the increase in the specific surface area of the carrier.

As described above, when a supported catalyst is produced, the specific surface area of the produced catalyst is known to become smaller than that of the carrier for producing the catalyst. Similar to the case of the catalyst according to the invention (I), the specific surface area of the catalyst as measured by a BET method varies in accordance not only with the surface area of the carrier but also with the amounts of a heteropoly acid and a salt thereof caused to be held on the carrier per unit volume of the carrier.

In general, the greater the amount of a catalyst component caused to be held on the carrier, the smaller the specific surface area of the obtained catalyst according to the invention (I). As a result, the apparent catalytic activity, i.e., the space-time yield of an ester, increases. In contrast, the selectivity of the ester decreases. Although the optimum range of the amount might be presumed on the basis of a balance between yield and selectivity, the range has not been elucidated at present.

Other properties of the carrier of the catalyst according to the invention (II) may be similar to those described in relation to the invention (I).

The process for producing the catalyst according to the invention (III) will next be described.

The present invention (III) provides a process for producing the catalyst as recited in the invention (I) or (II) used for producing a lower fatty acid ester.

Accordingly, the catalyst as recited in the invention (I) or (II) can be produced by a process comprising the following two steps.

First step:
A step of obtaining a solution or a suspension of a heteropoly acid and/or a salt thereof.

Second step:
A step of causing the solution or suspension obtained in the first step to be held on a carrier, to thereby obtain a catalyst for producing a lower fatty acid ester.

Firstly, the first step will be described.

The hetropoly acid or salt thereof used in the first step may be the same compound as described in relation to the invention (I).

The first step is a step for dissolving or suspending a heteropoly acid or a salt thereof in a solvent.

No particular limitation is imposed on the solvent which can be used in the first step, so long as the solvent can homogeneously dissolve or uniformly suspend the objective heteropoly acid or salt thereof. Examples of the solvents include water, organic solvent, and a mixture thereof. Non-limiting examples of preferred solvents include water, alcohol, and carboxylic acids.

No particular limitation is imposed on the method for dissolving or suspending the heteropoly acid or salt thereof; any method may be employed so long as the solvent can homogeneously dissolve or uniformly suspend the objective heteropoly acid or salt thereof.

Specifically, a heteropoly acid, i.e., free acid, may be dissolved in a solvent if it can be dissolved. Alternatively, if the acid is not completely dissolved, the acid may be suspended in a solvent through transformation into powder thereof or the like. Moreover, the heteropoly acid and a heteropoly acid-neutralizing salt are dissolved together or individually dissolved in a solvent, followed by mixing the resultant solution, to thereby prepare a homogeneous solution or suspension of a corresponding heteropoly acid salt. When a heteropoly acid salt is used, a homogeneous solution or suspension of the salt can be obtained in a manner similar to that described in relation to the heteropoly acid.

Although the optimum volume of the solution or suspension depends on the method for causing them to be held on the carrier in the second step or on the carrier which is employed in the second step, the optimum volume of the solution or suspension is not particularly limited.

Secondly, the second step will be described.

The carrier used in the second step may be the same one as described in relation to invention (I).

The second step is a step for causing the solution or suspension of a heteropoly acid or salt thereof obtained in the first step to be held on the carrier, to thereby obtain a catalyst for producing a lower fatty acid ester.

No particular limitation is imposed on the method for causing the solution or suspension of the heteropoly acid or salt thereof to be held on the carrier, and any known method may be employed.

For example, a heteropoly acid or salt thereof is dissolved or suspended in a solvent so as to form a solution or suspension in an amount corresponding to the amount which the carrier is able to absorb. The carrier is impregnated with the thus prepared solution or suspension, to thereby cause the solution or suspension to be held on the carrier.

In this case, the amount of liquid which the carrier can absorb must be measured in advance. For example, a specific amount of the carrier is weighed, and the weighed portion is placed in a container such as a beaker. Subsequently, pure water is added thereto such that the carrier is completely immersed in water. The mixture is allowed to stand at room temperature for 30 minutes or longer. Since the carrier absorbs a certain amount of water, pure water may be added excessively so as to avoid the occurrence of immersion failure in that a part of the carrier is not immersed in water or may be added continuously so as to maintain a state of complete immersion of the carrier in water.

Subsequently, the supernatant is removed from the mixture and residual water is removed from the carrier. The water-absorbed carrier is weighed. The difference between the weight of the carrier before absorption of pure water and that after absorption of pure water represents the weight of pure water absorbed by the carrier. If the specific gravity of pure water is one, the obtained weight directly represents the amount (volume) of liquid absorbed by the carrier which is measured. Thus, the optimum volume of the solution or suspension which is prepared in the first step can be determined by the amount of liquid and the amount of the employed carrier.

Alternatively, the supported catalyst may be prepared through the steps of suitably shaking the carrier in a heteropoly acid-containing solution or suspension in an excess amount to thereby impregnate the carrier with the component and removing the residual acid through filtration. The amount of liquid absorbed by the carrier also must be measured in the aforementioned manner. The concentration of a heteropoly acid or a salt thereof in the solution or suspension to be prepared is determined by the measured amount of liquid and the amount of the heteropoly acid or salt thereof which is caused to be held on the carrier. The thus obtained wet catalyst is suitably dried in a heating oven for several hours, and subsequently cooled to ambient temperature in a desiccator. A drying temperature in excess of 400° C. is not preferred, since degradation of the skeleton of a heteropoly acid is induced at such a temperature. The drying temperature is preferably 80° C.–350° C.

In industrial scale production, the above stationary drying apparatus may be substituted by a drying apparatus such as a roto-louvre drying apparatus, a continuous fluidized bed drying apparatus, or a continuous drying apparatus using hot gas, to thereby perform drying in a continuous manner.

The amount of a heteropoly acid held on the carrier can be calculated easily through subtraction of the weight of the employed carrier from that of the prepared catalyst in a dried state. The amount may be measured with higher precision through chemical analysis, such as ICP.

Finally, the present invention (IV) will be described.

The invention (IV) provides a process for producing a lower fatty acid ester through esterification of a lower aliphatic carboxylic acid with a lower olefin in the presence of the catalyst as recited in the invention (I) or (II).

Non-limitative examples of lower olefins which are used in the invention (IV) include ethylene, propylene, n-butene, isobutene, and a mixture thereof.

No particular limitation is imposed on the lower aliphatic carboxylic acid which is used in the invention (IV), and a $C_1$–$C_4$ aliphatic carboxylic acid is preferred. Examples include formic acid, acetic acid, propionic acid, acrylic acid, and methacrylic acid, with acetic acid and acrylic acid being particularly preferred.

The lower olefin is preferably used in equimolar amount or in an excessive amount with respect to the carboxylic acid. The molar ratio of the olefin to the carboxylic acid is preferably 1:1 to 30:1, more preferably 10:1 to 20:1.

The reaction comprising the use of the catalyst is carried out in a gaseous phase in any manner, such as a fixed bed method or a fluidized bed method and, in accordance with the mode of reaction, the form of the carrier may be chosen from powder and a shaped body having a size of several mm.

Preferably, a small amount of water is added to the raw materials in view of the service life of the catalyst. However, addition of an excessive amount of water disadvantageously induces an increase in ethanol and diethyl ether as by-products. Typically, water is added in an amount of 1 mol %–15 mol %, preferably 3 mol %–8 mol %, based on the total amounts of the lower olefin and the lower aliphatic carboxylic acid which are used in the reaction.

The reaction temperature and pressure are selected such that supplied media maintain a gaseous state, and vary depending on the raw materials. The reaction temperature is typically 120° C. to 250° C., more preferably 140° C. to 220° C.

The reaction pressure is typically from ordinary pressure to 2 MPa, more preferably from ordinary pressure to 1 MPa.

The raw materials are preferably supplied onto a catalyst layer formed of the catalyst, at a space velocity (GHSV) of 100/hour–7000/hour, more preferably 300/hour–2000/hour.

Ethanol and diethyl ether, which are by-products of the reaction, may be recycled together with ethylene.

The present invention will be described below by way of examples and comparative examples, which should not be construed as limiting the invention thereto.

Catalyst Preparation Example 1

First, the amount of liquid which the catalyst carrier can absorb was measured. 250 ml of CARiACT Q-30 (silica particles of 5–10 mesh; product of Fuji Silysia Chemical Ltd.) was placed in a 500-ml beaker. 300 ml of pure water was added thereto, and the mixture was allowed to stand for approximately 30 minutes at room temperature. The resultant supernatant was removed from the mixture and residual water was removed from the carrier. The pure water-absorbed carrier was weighed. The difference between the weight of the carrier before absorption of pure water and that after absorption of pure water represents the weight of pure water absorbed by the carrier. If the specific gravity of pure water is one, the obtained weight directly represents the amount (volume).

75 g of Commercially available phosphotungstic acid (product of Wako Pure Chemicals Industries Ltd.) (the weight including no crystal water) and 40 ml of pure water were placed in a 200-ml beaker to prepare a solution. Pure water was added thereto such that the volume of the aqueous solution of phosphotungstic acid became 98% of the above-measured amount of liquid absorbed by the carrier. The aqueous solution was completely absorbed in 250 ml of the above carrier. The phosphotungstic acid-held carrier was transferred to a porcelain dish (250 mmΦ) and dried in the air for three hours. Subsequently, the carrier was placed in a hot air dryer and dried in air at atmospheric pressure at 150° C. for five hours, to thereby obtain 183 g of catalyst 1.

The BET specific surface area of the thus prepared catalyst 1 and that of the carrier used for preparing catalyst 1 were measured by use of a gas adsorption instrument (SORPTMATIC 1990; FISTONS Instruments Co.). The samples were degassed in advance at 110° C. for two hours, and measurement was carried out at the temperature of liquid nitrogen (77K) by use of nitrogen gas as a measuring gas. The results are shown in Table 1.

TABLE 1

| Catalyst | Catalyst component | BET specific surface area (m²/g) Carrier | BET specific surface area (m²/g) Catalyst |
|---|---|---|---|
| Catalyst 1 | phosphotungstic acid | 113 | 76 |
| Catalyst 2 | phosphotungstic acid | 203 | 135 |
| Catalyst 3 | phosphotungstic acid | 286 | 195 |
| Catalyst 4 | phosphotungstic acid | 372 | 233 |
| Catalyst 5 | phosphotungstic acid | 286 | 261 |
| Catalyst 6 | phosphotungstic acid | 286 | 160 |
| Catalyst 7 | silicotungstic acid | 286 | 258 |
| Catalyst 8 | silicotungstic acid | 286 | 184 |
| Catalyst 9 | silicotungstic acid | 286 | 152 |
| Catalyst 10 | phosphotungstic acid | 142 | 94 |
| Catalyst 11 | phosphotungstic acid | 64 | 55 |
| Catalyst 12 | phosphotungstic acid | 588 | 375 |

Catalyst Preparation Example 2

The procedure for producing catalyst 1 was repeated, except that CARiACT Q-15 (silica particles of 5–10 mesh; product of Fuji Silysia Chemical Ltd.) was used instead of CARiACT Q-30, to thereby obtain 185 g of catalyst 2. The BET specific surface area of catalyst 2 and that of the carrier used for preparing catalyst 2 are shown in Table 1.

Catalyst Preparation Example 3

The procedure for producing catalyst 1 was repeated, except that CARiACT Q-10 (silica particles of 5–10 mesh; product of Fuji Silysia Chemical Ltd.) was used instead of CARiACT Q-30, to thereby obtain 188 g of catalyst 3. The BET specific surface area of catalyst 3 and that of the carrier used for preparing catalyst 3 are shown in Table 1.

Catalyst Preparation Example 4

The procedure for producing catalyst 1 was repeated, except that CARiACT Q-6 (silica particles of 5–10 mesh; product of Fuji Silysia Chemical Ltd.) was used instead of CARiACT Q-30, to thereby obtain 239 g of catalyst 4. The BET specific surface area of catalyst 4 and that of the carrier used for preparing catalyst 4 are shown in Table 1.

Catalyst Preparation Example 5

The procedure for producing catalyst 3 was repeated, except that phosphotungstic acid (product of Wako Pure Chemicals Industries Ltd.) was used in an amount of 25 g, to thereby obtain 139 g of catalyst 5. The BET specific surface area of catalyst 5 and that of the carrier used for preparing catalyst 5 are shown in Table 1.

Catalyst Preparation Example 6

The procedure for producing catalyst 3 was repeated, except that phosphotungstic acid (product of Wako Pure Chemicals Industries Ltd.) was used in an amount of 125 g, to thereby obtain 235 g of catalyst 6. The BET specific surface area of catalyst 6 and that of the carrier used for preparing catalyst 6 are shown in Table 1.

Catalyst Preparation Example 7

The procedure for producing catalyst 3 was repeated, except that silicotungstic acid (product of Wako Pure Chemicals Industries Ltd.) was used in an amount of 25 g (the weight including no crystal water) instead of phosphotungstic acid (product of Wako Pure Chemicals Industries Ltd.), to thereby obtain 137 g of catalyst 7. The BET specific surface area of catalyst 7 and that of the carrier used for preparing catalyst 7 are shown in Table 1.

Catalyst Preparation Example 8

The procedure for producing catalyst 3 was repeated, except that silicotungstic acid (product of Wako Pure Chemicals Industries Ltd.) was used in an amount of 75 g (the weight including no crystal water) instead of phosphotungstic acid (product of Wako Pure Chemicals Industries Ltd.), to thereby obtain 188 g of catalyst 8. The BET specific surface area of catalyst 8 and that of the carrier used for preparing catalyst 8 are shown in Table 1.

Catalyst Preparation Example 9

The procedure for producing catalyst 3 was repeated, except that silicotungstic acid (product of Wako Pure Chemicals Industries Ltd.) was used in an amount of 125 g (the weight including no crystal water) instead of phosphotungstic acid (product of Wako Pure Chemicals Industries Ltd.), to thereby obtain 239 g of catalyst 9. The BET specific surface area of catalyst 9 and that of the carrier used for preparing catalyst 9 are shown in Table 1.

Catalyst Preparation Example 10

The procedure for producing catalyst 1 was repeated, except that KA-1 (5 mm silica balls; product of Sued Chemie Co.) was used instead of CARiACT Q-30, to thereby obtain 216 g of catalyst 10. The BET specific surface area of catalyst 10 and that of the carrier used for preparing catalyst 10 are shown in Table 1.

Catalyst Preparation Example 11

The procedure for producing catalyst 1 was repeated, except that CARiACT Q-50 (silica particles of 5–10 mesh; product of Fuji Silysia Chemical Ltd.) was used instead of CARiACT Q-30, to thereby obtain 181 g of catalyst 11. The BET specific surface area of catalyst 11 and that of the carrier used for preparing catalyst 11 are shown in Table 1.

Catalyst Preparation Example 12

The procedure for producing catalyst 1 was repeated, except that CARiACT Q-3 (silica particles of 5–10 mesh; product of Fuji Silysia Chemical Ltd.) was used instead of CARiACT Q-30, to thereby obtain 292 g of catalyst 12. The BET specific surface area of catalyst 9 and that of the carrier used for preparing catalyst 9 are shown in Table 1.

Example 1

Catalyst 1 obtained in Catalyst Preparation Example 1 was charged in a 40-ml reaction tube, and a mixed gas having the following proportions by volume: ethylene:acetic acid:steam:nitrogen=78.5:8.0:4.5:9.0 was introduced thereto at a flow rate of 60 Nl/H, a temperature of 165° C., and a pressure of 0.8 MPaG, to thereby carry out the reaction.

Three to five hours after initiation of reaction, the resultant gas was sampled at the outlet of the reaction tube. Sampling was carried out through the steps of cooling the resultant gas flowing in the outlet portion of the reaction tube to condense; collecting the total amount of the condensed reaction mixture; and analyzing through gas chromatography (by use of a GC-14B, product of Shimadzu Corporation). The amount of the break-through gas which had not condensed was obtained by measuring the flow rate in the outlet portion of the reaction tube during sampling, and a portion of the gas was analyzed through gas chromatography (by use of a GC-14B and a GC-7A, products of Shimadzu Corporation), to thereby obtain the composition of the gas.

Nitrogen contained in the break-through gas was analyzed under the following conditions: a gas chromatograph (GC-7A, product of Shimadzu Corporation) equipped with a gas sampler for gas chromatography (MGS-4, product of Shimadzu Corporation, measuring tube 1 ml); a packed column containing Molecular Sieve 5A (3 m); helium serving as a carrier gas (flow rate of 45 ml/min); temperature of the detection chamber 130° C.; temperature of the vaporization chamber 110° C.; column temperature of 60° C., constant; and TCD detector (current: 100 mA). An absolute calibration curve method was employed for analysis. The break-through gas was collected in a volume of 50 ml, and the total amount of the gas was caused to flow to the gas sampler. The last 1 ml was subjected to analysis.

Non-condensed diethyl ether, ethyl acetate, and ethanol were analyzed under the following conditions: a gas chromatograph (GC-14B, product of Shimadzu Corporation) equipped with a gas sampler for gas chromatography (MGS-4, product of Shimadzu Corporation, a measuring tube 1 ml); a packed column (SPAN 80 15% Shinchrom A 60–80 mesh (5 m); nitrogen serving as a carrier gas (flow rate of 25 ml/min); temperatures of the detector and the vaporization chamber 120° C.; column temperature of 65° C., constant; and FID detector ($H_2$ pressure 0.6 kg/cm , air pressure 1.0 kg/cm$^2$).

Each concentration of non-condensed diethyl ether, ethyl acetate, and ethanol was calibrated by the following method. By use of a micro-syringe, each component was sampled in a liquid state in a suitable amount selected within the range of 0.5 μl to 10 μl. Separately, a container which can be sealed (for example, a 200 ml-syringe having a cock for sealing) was filled with air (100 ml) at normal temperature and pressure. The component for analysis collected in the micro-syringe was injected thereto, and the container was sealed again. The injected component was completely vaporized as is or by heating once and allowing to stand to cool to normal temperature. By further feeding air, the total volume of the gas was adjusted to 200 ml at normal temperature and pressure. After the gas in the sealed container was sufficiently mixed, the gas was used as a standard gas, to carry out calibration. Analysis was conducted by an absolute calibration curve method. The break-through gas was collected in a volume of 50 ml, and the total amount of the gas was caused to flow to the gas sampler. The last 1 ml was subjected to analysis.

If the balance of the break-through gas was ethylene, except for the components measured through the above two gas chromatographic analysis steps, the amount of each component in the break-through gas during sampling was obtained through measurement of the volume of the break gas during sampling.

The collected reaction mixture was analyzed under the following conditions: a gas chromatograph (GC-14B, product of Shimadzu Corporation); a capillary column TC-WAX (length 30 m, inner diameter 0.25 mm, film thickness 0.25 μm); nitrogen serving as a carrier gas (split ratio 20, flow rate of 2 ml/min); nitrogen serving as a make-up gas (flow rate of 35 ml/min); temperatures of the detector and the vaporization chamber 200° C.; column temperature; 50° C. (constant for five minutes from the beginning), elevation to 150° C. (at 20° C./minute), and 150° C. (constant, for ten minutes); and FID detector ($H_2$ pressure 0.6 kg/cm , air pressure 1.0 kg/cm$^2$). An inner standard method was employed for analysis. Thus, 1,4-dioxane (1 ml) was added to the reaction mixture (10 ml) as an internal standard, and the resultant mixture (0.2 ml) was injected for analysis.

The results obtained from analyses of the break-through gas and the collected reaction mixture are shown in Table 2.

TABLE 2

| | | Space-time | Selectivity (%) | | |
| --- | --- | --- | --- | --- | --- |
| | Catalyst | yield g/l-cat · h | ethyl acetate | diethyl ether | ethanol |
| Example 1 | Cat. 1 | 113 | 96.46 | 0.33 | 3.21 |
| Example 2 | Cat. 2 | 239 | 91.56 | 3.80 | 4.64 |
| Example 3 | Cat. 3 | 251 | 89.68 | 5.72 | 4.59 |
| Example 4 | Cat. 4 | 172 | 94.75 | 1.45 | 3.80 |
| Example 5 | Cat. 5 | 116 | 96.72 | 1.03 | 2.25 |
| Example 6 | Cat. 6 | 292 | 86.61 | 9.18 | 4.21 |
| Example 7 | Cat. 7 | 121 | 95.53 | 1.12 | 3.35 |
| Example 8 | Cat. 8 | 256 | 90.61 | 4.68 | 4.71 |
| Example 9 | Cat. 9 | 308 | 85.42 | 9.46 | 5.40 |
| Example 10 | Cat. 10 | 181 | 92.41 | 3.65 | 3.94 |
| Comp. Ex. 1 | Cat. 11 | 75 | 96.72 | 0.17 | 3.11 |
| Comp. Ex. 2 | Cat. 12 | 2 | 100.00 | 0.00 | 0.00 |

Examples 2–10

Catalysts 2–10 obtained in Catalyst Preparation Examples 2–10 were used for reaction and analyzed in the same manner as in Example 1. The results are shown in Table 2.

Comparative Examples 1 and 2

Catalysts 11 and 12 obtained in Catalyst Preparation Examples 11 and 12 were used for reaction and analyzed in the same manner as in Example 1. The results are shown in Table 2.

As described above, the catalyst of the present invention having a specific surface area as measured by BET method of 65 m$^2$/g–350 m$^2$/g and the process for producing a lower fatty acid ester by using the catalyst enable production of a lower fatty acid ester with higher efficiency as compared with a conventional catalyst and process.

What is claimed is:

1. A process for producing a $C_{1-4}$ aliphatic carboxylic acid ester, comprising esterifying a $C_{1-4}$ aliphatic carboxylic acid with a $C_{1-4}$ olefin in the presence of a catalyst which contains at least one compound selected from heteropoly acids and salts thereof, which compound is caused to be held on a silica carrier, wherein the specific surface of the catalyst as measured by BET method is 65 m$^2$/g–350 m$^2$/g.

2. A process according to claim 1, wherein the $C_{1-4}$ aliphatic carboxylic acid is esterifying with a $C_{1-4}$ olefin in the presence of water.

3. A process according to claim 1, wherein the $C_{1-4}$ aliphatic carboxylic acid is selected from the group consisting of formic acid, acetic acid, propionic acid, acrylic acid and methacrylic acid.

4. A process according to claims 1, wherein the $C_{1-4}$ olefin is selected from the group consisting of ethylene, propylene, n-butene and isobutene.

5. The process according to claim 1, wherein the silica carrier comprises silica having a purity of 95 wt % or more as represented by weight ratio based on the total weight of the carrier.

6. The process according to claim 1, wherein the heteropoly acids are elected from the group consisting of silicotungstic acid, phosphotungstic acid, phosphomolybdic acid, silicomolybdic acid and phosphovanadomolybdic acid.

7. The process according to claim 1, wherein the heteropoly acids are selected from the group consisting of lithium, sodium, potassium, cesium, magnesium, barium, copper, gold, gallium and ammonium salts of an acid selected from silicotungstic acid, phosphotungstic acid, phosphomolybdic acid, silicomolybdic acid and phosphovanadomolybdic acid.

8. The process according to claim 1, wherein the specific surface area of the carrier as measured by BET method is 100 m2/g to 500 $m^2/g$.

* * * * *